United States Patent [19]

D'Angelo et al.

[11] 3,963,673
[45] June 15, 1976

[54] POLYMER CROSSLINKING WITH COUPLED PEROXIDES

[75] Inventors: Antonio Joseph D'Angelo, Buffalo; Orville Leonard Mageli; Chester Stephen Sheppard, both of Kenmore, all of N.Y.

[73] Assignee: Pennwalt Corporation, Philadelphia, Pa.

[22] Filed: June 25, 1974

[21] Appl. No.: 482,942

Related U.S. Application Data

[62] Division of Ser. No. 342,106, March 16, 1973, Pat. No. 3,846,396, which is a division of Ser. No. 737,359, June 17, 1968, Pat. No. 3,725,455.

[52] U.S. Cl. .................. 260/46.5 G; 260/47 XA; 260/75 T; 260/77.5 A; 260/785 C; 260/80.78; 260/85.1; 260/85.3 C; 260/86.1 E; 260/87.3; 260/88.2 C; 260/92.3; 260/92.8 A; 260/93.7; 260/94.8; 260/768 R; 260/861; 526/12; 526/19; 526/20; 526/23; 526/55; 526/57; 526/193; 526/230; 526/279; 526/304; 526/310; 526/319; 526/340; 526/350

[51] Int. Cl.² .................. C08F 8/00; C08F 210/16; C08G 18/86; C08J 3/24

[58] Field of Search ..... 260/46.5 G, 75 TN, 75 NY, 260/77.5 AP, 77.5 A, 88.2 C, 80.78, 85.1, 94.8, 47 XA, 75 T, 78 SC, 92.3, 92.8 A, 85.3, 93.7, 86.1 E, 87.3, 768, 861

[56] References Cited
UNITED STATES PATENTS

| | | | |
|---|---|---|---|
| 3,658,914 | 4/1972 | Gregory | 260/610 R |
| 3,678,014 | 7/1972 | Suzuki et al. | 260/77.5 CR |
| 3,681,316 | 8/1972 | Schappell | 260/94.9 GA |

*Primary Examiner*—Donald E. Czaja
*Assistant Examiner*—E. A. Nielsen

[57] ABSTRACT

A new class of compounds: R-W-R' where R and R' are identical oxy radicals containing peroxide functions such as dialkyl or diaralkyl peroxide, proxyketal, peroxyester, or monoperoxycarbonate, and W is a carbonyl group, or carbonyl containing group, or an alkylidene or aralkylidene group, or a phosphorous containing group.

Examples:
  Di[1,3-dimethyl-3-(t-butylperoxy)butyl]carbonate;
  Di[1,3-dimethyl-3-(n-butoxycarbonylperoxy)butyl]-carbonate;
  2,2-Bis[3,3-di(t-butylperoxy)butyoxy]propane;
  Di[1,3-dimethyl3-(t-butylperoxy)butyl]ethyl phosphate.

They are free radical affording compounds useful in crosslinking of polyolefins and unsaturated polymers, and for the polymerization of vinyl monomers and diolefinic monomers.

11 Claims, No Drawings

POLYMER CROSSLINKING WITH COUPLED PEROXIDES

This is a division, of application Ser. No. 342,106, filed Mar. 16, 1973, which in turn is a division of application Ser. No. 737,359, filed June 17, 1968 (now U.S. Pat. No. 3,725,455).

BACKGROUND OF THE INVENTION

1. The Field of the Invention

This invention relates to peroxides obtainable by the coupling of hydroxide group containing peroxides. Particularly the invention relates to coupled peroxide containing one or more carbonyl groups or an alkylidene group in the portion of the molecule which forms the linkage between the two peroxy containing portions of the coupled peroxide molecule. Also the invention relates to methods for preparing such coupled peroxides.

2. Description of the Prior Art

No prior art is known with respect to the coupled peroxides of the invention.

U.S. Pat. No. 3,236,872 discloses dialkyl peroxides containing hydroxyl groups, e.g., 2-methyl-2-(t-butylperoxy)-4-pentanol.

A copending application, Ser. No. 569.030, filed Aug. 1, 1966 (now U.S. Pat. No. 3,542,856) discloses peroxyesters containing hydroxyl groups, e.g., t-butylperoxy-3-hydroxypropionate.

Still other precursors, hydroxy substituted peroxyketals are disclosed in a copending application, Ser. No. 727,336 filed May 7, 1968, e.g., 3,3-Bis(t-butylperoxy)-1-butanol.

SUMMARY OF THE INVENTION

It has been discovered that high purity polyfunctional peroxides, i.e., at least two peroxy groups, can be prepared by a coupling reaction carried out on a hydroxy group containing peroxide.

The novel polyfunctional peroxides of this invention have the general formula:

$$R—W—R'$$

where:

1. R and R' are identical, and each contain at least one peroxy (—OO—) group selected from the class consisting of:

   i

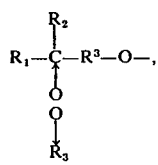   ii

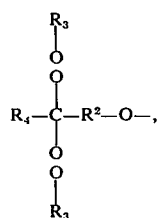   iii

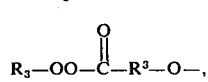   iv

   iv

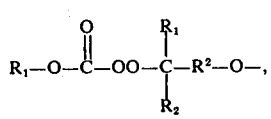   v and

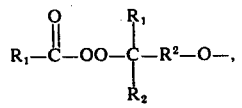   vi where R and R' each fall into the same member (i)–(vi) respectively and the $R_1$, $R_2$, $R_3$, $R_4$, $R^2$, $R^3$, and $R^4$ required to be present in the particular R' is the same as the corresponding radical [i.e., $R_1$, $R_2$, $R_3$, $R_4$, $R^2$, $R^3$, and $R^4$ as the case may be] required to be present in the corresponding R. To illustrate: If R is:

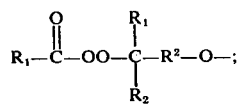

then R' is also:

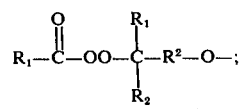

and $R_1$, $R_2$, and $R^2$ are identical in both R and R'.

2. W is a diradical selected from the class consisting of:

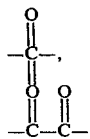   i ii

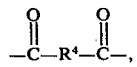   iii

   iv and

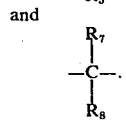   v

3. $R_1$ and $R_2$ are aliphatic having 1–12 carbon atoms, cycloaliphatic having 3–12 carbon atoms, or aromatic having 6–12 carbon atoms;

4. $R_3$ is aliphatic or cycloaliphatic, each having 4–10 carbon atoms and the carbon atom joined to the peroxy oxygen atom is a tertiary carbon atom;

5. $R_4$ is aliphatic having 1–10 carbon atoms or cycloaliphatic having 3–12 carbon atoms;

6. $R_5$ is lower alkyl, cycloalky, aralkyl, aryl, alkoxy, cycloalkoxy, aralkoxy, or aryloxy;

7. $R_6$ is H or lower alkyl;

8. Y is the diradical O, S, or N—$R_6$;

9. R² is an aliphatic diradical having 1–10 carbon atoms or a cycloaliphatic diradical having 3–12 carbon atoms;
10. R³ is an aliphatic diradical having 1–10 carbon atoms, cyloaliphatic diradical having 3–12 carbon atoms, or aromatic diradical having 6–12 carbon atoms;
11. R₇ and R₈ are selected from the class consisting of H, alkyl of 1–10 carbons and cycloalkyl of 3–12 carbons and when R₇ is H, R₈ can also be aryl of 6–12 carbons and R₇ and R₈ can together form an alkylene biradical of 2–11 carbons; and
12. R⁴ is a diradical selected from the class consisting of:

R³  The i

YR³Y The ii

 iii

 iv

 v

 vi

 vii

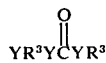 viii

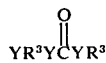 ix

YR³YR³Y x

Illustrative peroxides are:
Di[1,3-dimethyl-3-(t-butylperoxy)butyl] carbonate.
Di[4,4-di(t-butylperoxy)pentyl] carbonate.
Di[1,3-dimethyl-3-(t-butylperoxy)butyl] succinate.
Ethylene Bis[1,3-dimethyl-3-(t-butylperoxy)-butyl carbonate].
Di[1,3-dimethyl-3-(t-butylperoxy)butyl] ethyl phosphate.
2,2-Bis[3,3-di(t-butylperoxy)butoxy]propane.
N,N'-m-phenylene bis[O-[1,3-dimethyl-3m(t-butylperoxy)butyl]carbamate].

DESCRIPTION OF THE INVENTION AND EXAMPLES

The aliphatic radical includes substitution by aryl radicals — araliphatic radicals — and cycloaliphatic radicals. The cycloaliphatic radical includes substitution by aliphatic and by aryl radicals. The aromatic and aryl radicals may be substituted by aliphatic and by cycloaliphatic radicals. Both cycloaliphatic, aromatic and aryl radicals may be single ring, such as phenyl and cyclohexyl, or connected rings, such as biphenyl, binaphthyl, bicyclopropyl, bicyclopentyl, or fused rings such as naphthyl, decahydronaphthyl. It is to be understood that the substituents should not interfere with the desired coupling reaction. In general halogen, ester, ether, thioether, and carbonate substituents or groups containing these do not interfere. Desirably R₁, R₂, R₃, R₄, R², R³, and R⁴ contain only carbon and hydrogen atoms.

Commonly R₅ is alkyl or alkoxy having 1–6 carbon atoms; cycloalkyl or cycloalkoxy having a total of 3–12 carbon atoms; aralkyl or aralkoxy having 7–12 carbon atoms; aryl or aryloxy having 6–12 carbon atoms.

Commonly, R₆ is H or alkyl having 1–4 carbon atoms.

Commonly R₇ and R₈ are each H or alkyl having 1–4 carbon atoms or one can be aryl while the other is H or R₇ and R₈ together can form an alkylene biradical.

R₃ is an aliphatic or cycloaliphatic radical, each having 4–10 carbon atoms, affording a t-carbon atom which is joined to a peroxy oxygen atom. For example.

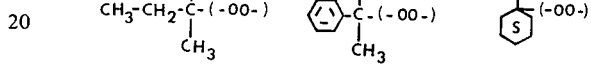

The described coupled peroxy compounds are effective crosslinking agents for polymeric materials which are capable of being crosslinked to form a thermoset material.

Illustrative classes of polymeric materials where these new peroxy compounds are effective include: homopolymers, such as poly(vinyl chloride) and polyolefins (e.g. polyethylene and polybutenes); elastomers, such as natural rubber and synthetic rubber (e.g. butyl rubber, GR-S rubbers, neoprene, acrylic rubber, Buna rubber, ethylene-propylene rubber, silicone rubbers, and miscellaneous elastomeric material such as polybutene-styrene copolymers and polyurethane rubber), copolymers such as poly(ethylene-vinyl acetate) and condensation polymers such as polyamides, polyesters (both saturated and unsaturated) and polycarbonates. The polymer may contain a plasticizer and/or oil extenders and/or fillers such as carbon black, silica and calcium carbonate. Also they are effective in curing (crosslinking) mixtures of vinyl monomers and unsaturated polyesters.

Also they are effective for the polymerization, to form solid polymers, of unsaturated monomers capable of polymerization by a free radical mechanism. For example, vinyl monomers such as vinyl halides; vinylidene halides; vinyl esters such as vinyl acetate and vinyl stearate; the vinyl toluene; the acrylics such as acrylic acid, methyl methacrylate and ethyl acrylate. Other monomers are: The styrene-butadiene blends for rubber copolymers; styrene-acrylonitrile blends for copolymers; fluoroethylenes and chloro-fluoroethylenes; butadiene; isoprene and similar polymerizable dienes.

Utility and Discussion

These novel coupled peroxycompounds can be utilized in the following ways:
1. They can crosslink polyethylene, polyethylene-polypropylene rubber, polyolefin elastomers, polyurethane rubbers, silicon rubber etc. (Example XIII, Tables I, II, III and IV)
2. They can polymerize monomers containing polymerizable ethylenic grouping. (Example XIV)
3. They can cure resins curable by free radical producing agents. (Example XV)

4. They can be used as free radical sources and/or catalysts in organic syntheses and applications where free radicals are required.

Some of the desirable properties that a peroxide has to have to be useful for crosslinking polyethylene are: low volatility, high thermal stability, and good efficiency with respect to its active oxygen content.

The volatility and the thermal stability are necessary requisites, since the peroxide has to tolerate the high temperatures of the milling operation, which is a necessary step to incorporate the peroxide with the polymer before the crosslinking process. If the peroxide is too volatile (as in the case of di-t-butyl peroxide) there would not be any peroxide left for the crosslinking process at the end of the milling step. If the peroxide is not volatile, but its thermal stability is low, a premature decomposition of the peroxide will take place during the milling step, which results in a premature crosslinking of the polymer. If this happens, the polymer cannot be shaped or formed any further since the thermoplastic polymer has become thermoset too soon.

Efficiency is another property that a good crosslinking peroxide has to have in order to make the crosslinking process economical and effective.

Another advantage of the difunctional peroxides obtained by the coupling reaction is that they utilize their active oxygen content to the full extent. Some of the known commercial difunctional peroxides like 2,5-dimethyl-2,5-di(t-butylperoxy)hexane and 2,5-dimethyl-2,5-di(t-butylperoxy)-hexyne-3 are not as efficient in utilizing their active oxygen content as the difunctional peroxide of our invention (see Table I). This is an unexpected result.

We have demonstrated that hydroxy containing peroxides, such as 2-methyl-2-(t-butylperoxy)-4-pentanol, do not have all the desirable properties of a good crosslinking agent. Its volatility is low and its thermal stability is good, but its efficiency is poor. (see Table I)

By coupling this hydroxy containing peroxide, using the process described in Examples I, II, and III, we found the coupled product to be an exceptionally good crosslinking agent possessing all the desirable properties. (see Table I)

[The half-life of the coupled products (e.g. from Examples I, II, III, and V) is almost double that of the hydroxy containing peroxide precursors. This, to say the least, is unexpected.] (see Example XVI)

[Another advantage of the coupling reaction is the simplicity of preparing pure difunctional peroxides without going through tedious purification steps that are necessary when they are prepared peroxidizing difunctional intermediates.]

The coupling reaction is not the only expedient one can use to improve volatility of the hydroxy containing peroxides. One can acylate the hydroxyl group with a sufficiently high molecular weight acylating agent and the volatility will be reduced. Using too low of a molecular weight acylating agent will not lower volatility sufficiently unless the starting hydroxy-containing peroxide is already of substantial molecular weight.

The disadvantage of this approach is that an increase in the molecular weight of the peroxide is attained at a sacrifice of active oxygen content.

Peroxides are sold by the pound and used according to the active oxygen content. So, of one had to buy a high molecular weight product with small active oxygen content, larger amounts of the product would have to be used to obtain the desired results in that particular application.

The coupled compounds of our invention minimize this disadvantage, since they gave the desired properties without excessively increasing the molecular weight.

Thus, the coupling reactions of hydroxy-containing peroxides R—H, afford novel peroxides, R—W—R', that are unexpectedly more stable than R—H; more efficient than R—H and other commercial diperoxides; and at the same time are less volatile than R—H and simple derivatives of R—H.

PREPARATION

The hydroxy-containing peroxide precursors, R—H, can be prepared by peroxidation of intermediates containing hydroxyl groups, either primary or secondary, or by hydrolysis or reduction of ester-containing peroxides.

The novel peroxides, R—W—R', of this invention may be prepared by reacting the hydroxy-containing peroxides, R—H, with hydroxy coupling agents such as phosgene, diacid chlorides, bischloroformates, diisocyanates, dichlorophosphonates, aldehydes, and ketals.

The novel peroxides of this invention may be prepared by one or more of the following methods.

Method I (The One Step Process)

Two moles of the hydroxy-containing peroxide are reacted with one mole of the desired hydroxy-coupling agent to obtain R—W—R'.

Illustrative reactions are:

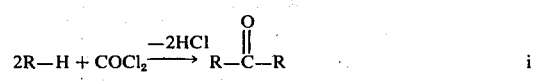  i

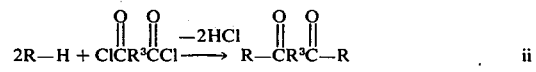  ii

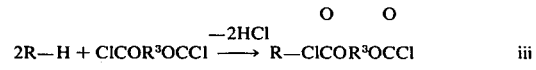  iii

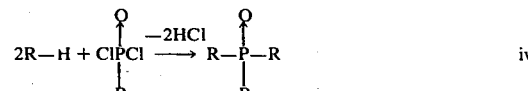  iv

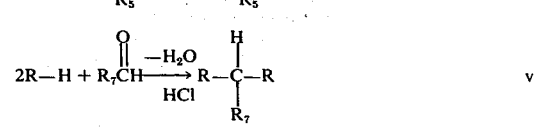  v

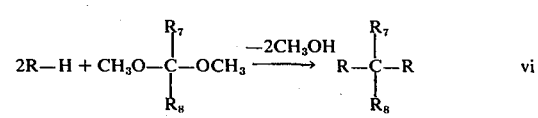  vi

Method II (The Two Step Process)

One mole of the hydroxy-containing peroxide is first reacted with one mole of hydroxy coupling agent to attain an intermediate product.

The preparation of certain of these intermediate products is disclosed in copending application Ser. No. 727,323 filed May 7, 1968 (now U.S. Pat. No. 3,671,651).

This intermediate product can subsequently be reacted with another mole of the hydroxy-containing peroxide in a second step to form R—W—R'.

Illustrative reactions are:

followed by

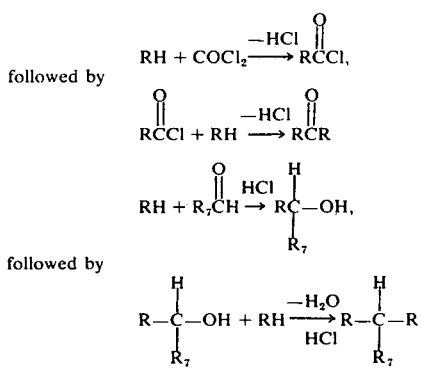

In other illustrative reactions when the intermediate product is a chloroformate-, or acid chloride-, or isocyanate-, or chlorophosphonate- containing peroxide, the intermediate can be reacted with other difunctional compounds such as diamines, diols, and dimercaptans in the second step to form R—W—R':

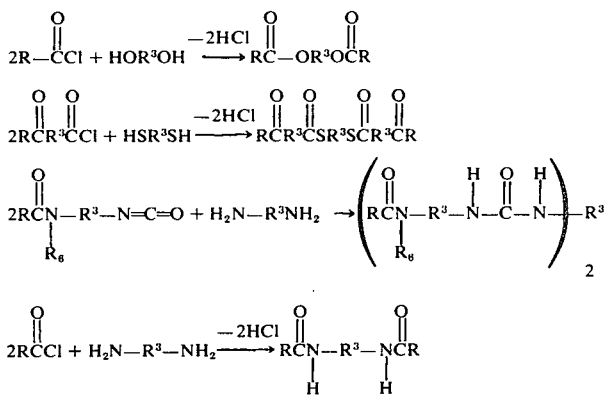

When the intermediate product is a chloroformate-containing peroxide, it can also be converted directly to R—W—R' in the second step, e.g.

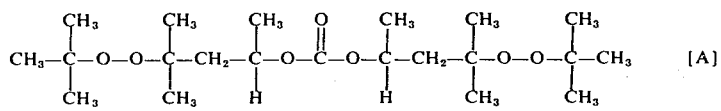

The reaction conditions depend upon the characteristics of the reactants and peroxy products. In general the intermixing of the coupling agent and the peroxy compound is carried out from about −10°C. to +25°C., and then the reaction temperature may be increased to a maximum of not more than 100°C., to allow the reaction to go to completion. Preferably the maximum reaction temperature should be not more than about 60°C.

The reactions may take place in the presence or absence of an inert diluent or solvent. In certain cases, where one or more of the reactants are solids, such a diluent is necessary to provide intimate contact of the reactants; in other cases the diluent provides an additional safety factor, as some pure products are hazardous.

In certain cases the presence of a base may be necessary i.e. Method I (i), (ii), (iii), and (iv) or Method II (a), (c), (d), and (f).

Any compound, inorganic or organic in nature, which functions as an acid acceptor (base) for the acid by-product of the reaction can be used.

Illustrative of organic bases are: pyridine, and substituted pyridines; lower alkyl tertiary amines such as trimethyl amine, and triethylamine; dimethyl aniline; and N-methyl-2-pyrrolidone.

Illustrative inorganic bases which can be used are the basic salts of alkali metals and alkaline earth metals such as sodium, and potassium carbonates, and sodium and potassium hydroxide.

The above methods of preparation of the novel peroxides, R—W—R', are further illustrated in Examples I to XII.

EXAMPLE I

Preparation of
Di[1,3-dimethyl-3-(t-butylperoxy)butyl] carbonate

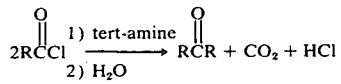

To a mixture of 22.6 g. (0.1 mole) of 2-methyl-2-(t-butylperoxy)-4-pentanol (84%) and 15.8 g. (0.2 mole) of pyridine in 50 ml. of hexane cooled to 5± 1°C. was added a solution of 5 g. (0.05 mole) of phosgene in 50 ml. of hexane.

The addition was made at such a rate that the reaction temperature could be controlled at 5± 1°C. After the addition was completed, the reaction temperature was allowed to rise to 23°–25°C., and then raised to 50± 1°C. by means of external heating. The reaction mixture was allowed to react for 48 hours at this temperature.

The reaction mixture was filtered from the pyridine hydrochloride and the organic phase washed with 10% tartaric acid solution and water to neutrality.

The organic phase was then dried over anhydrous magnesium sulfate, filtered and the solvent evaporated under reduced pressure. A slightly colored liquid was obtained, 20.1 g., theoretical 20.3 g. The infrared spectrum (I.R.) of this material showed presence of trace amounts of unreacted 2-methyl-2-(t-butylperoxy)-4-pentanol.

The unreacted material was distilled under reduced pressure at 34°–35°C. and 0.05 mm. of Hg. The I.R. of the residue was free of OH and contained the characteristic bands of the desired product.

EXAMPLE II

Preparation of [A]

To a solution of 27.2 g. (0.1 mole) of 1,3-dimethyl-3-(t-butylperoxy)butyl chloroformate (93.5%) (prepared from 2-methyl-2-(t-butylperoxy)-4-pentanol and phosgene) in 75 ml. of diethyl ether, cooled at 15± 1°C. was added a solution of 7.9 g. (0.1 mole) of pyridine in 25 ml. diethyl ether. The pyridine chloroformate complex separated at first and then dissolved, giving a pink colored solution. While the reaction temperature was controlled 15± 1°C., a solution of 22.6 g. (0.1 mole) of 2-methyl-2-(t-butylperoxy)-4-pentanol (84%) in 50 ml. of diethyl ether was added dropwise.

After the addition was completed, the mixture was allowed to reflux for twenty-four hours at 36± 1°C. At the end of this period the reaction mixture was filtered from the pyridine hydrochloride and washed with 10% solution of tartaric acid and water to neutrality. The ether solution was dried over anhydrous $MgSO_4$, filtered and the solvent evaporated under reduced pressure and then under vacuum at 0.1 mm. of Hg and a bath temperature of 60° to 70°C. A liquid was obtained (40 g.); theoretical yield 40.6 g.

The I.R. of this liquid was free of OH and C-Cl bands and contained the characteristic bands of the desired product.

EXAMPLE III

Preparation of [A]

To a solution of 29.2 g. (0.1 mole) of 1,3-dimethyl-3-(t-butylperoxy)butyl chloroformate (86.5%) in diethyl ether at 23± 1°C. was added a solution of 7.9 g. (0.1 mole) of pyridine in 10 ml. of diethyl ether. To this mixture was added dropwise 0.6 g. of $H_2O$ at such a rate that the evolution of $CO_2$ could be controlled to a reasonable rate. The reaction temperature rose to about 30°C. The reaction mixture was allowed to react at room temperature (23°C.) until the $CO_2$ evolution ceased (24 hours). The reaction mixture was diluted with $H_2O$ and the organic phase was separated, washed with 10% solution of tartaric acid and $H_2O$ to neutrality.

The ether solution was dried over anhydrous $MgSO_4$, filtered and the solvent evaporated under reduced pressure and then under vacuum at 0.1 mm. of Hg. and a bath temperature of 60°–70°C. A liquid was obtained 16.2 g.; theoretical yield 20.3 g.

The I.R. of this material was free of OH and C-Cl bands and contained the characteristic bands of the desired product.

EXAMPLE IV

Preparation of Di[4,4-di(t-butylperoxy)pentyl] carbonate

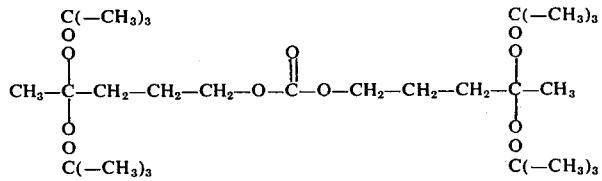

To a mixture of 8.0 g. (0.0295 mole) of 4,4-di(t-butylperoxy)-5-pentanol (97.3%), 2.4 g. (0.0295 mole) of pyridine in 50 ml. diethyl ether cooled at 5± 1°C. was added a solution of 1.45 g. (0.0147 mole) of phosgene in 25 ml. of diethyl ether. After the addition was completed, the reaction mixture was allowed to stir for six hours at 23± 1°C. After this time, the pyridine hydrochloride was filtered off and the ether solution was washed with 10% solution of tartaric acid and water to neutrality. The ether phase was dried over anhydrous $MgSO_4$, filtered and the solvent evaporated under reduced pressure. A liquid was obtained, 8.5 g.

The I.R. indicated that the desired product was obtained.

EXAMPLE V

Preparation of Di[2-(t-butylperoxycarbonyl)ethyl] carbonate

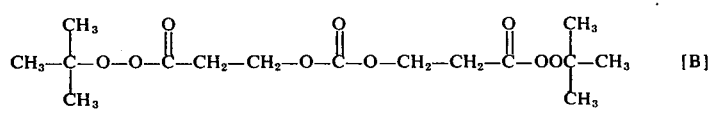

To a mixture of 17.4 g. (0.1 mole) of t-butyl 3-hydroxyperoxypropionate (93%) and 7.9 g. (0.1 mole) of pyridine in diethyl ether cooled at 5± 1°C. was added a solution of 30.5 g. (0.1 mole) of 2-(t-butylperoxycarbonyl)-ethyl chloroformate (75%) in 50 ml. of diethyl ether.

After the addition was completed the reaction mixture was allowed to stir for one hour at 30± 1°C. At the end of this period the reaction mixture was filtered off from the pyridine hydrochloride and the ether solution was washed with 10% solution tartaric acid and water to neutrality. The ether solution was dried over anhydrous $MgSO_4$, filtered and the solvent evaporated under reduced pressure. A colorless liquid was obtained (41 g.). The I.R. of this material showed the characteristic bands for the desired product.

EXAMPLE VI

Preparation of Di[1,3-dimethyl-3-(n-butoxycarbonylperoxy)-butyl] carbonate

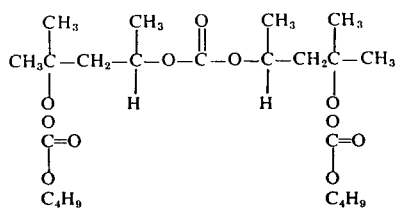

To a mixture of 26.0 g. (0.1 mole) of O,O-(1,1-dimethyl-3-hydroxybutyl) O-butyl monoperoxycarbonate (90%) and 7.9 g. (0.1 mole) of pyridine in 50 ml. of diethyl ether, cooled at 10± 1°C. was added a solution of 31.4 g. (0.1 mole) of 1,3-dimethyl-3-(n-butoxycarbonyl-peroxy)butyl chloroformate in 50 ml. of diethyl ether, at such a rate that the reaction could be controlled at 10± 1°C.

After the addition was completed, the reaction temperature was allowed to rise to 23°–25°C. and allowed to stir for one hour. At the end of this time, the reaction mixture was diluted with water and the organic phase separated and washed with 10% solution of tartaric acid and water to neutrality. The ether phase was dried over anhydrous magnesium sulfate, filtered and the solvent evaporated under reduced pressure and then under vacuum at 30° to 35°C. and 0.05 mm. of Hg. A liquid was obtained, 45.3 g.

The I.R. of this material indicated that the desired product was prepared.

EXAMPLE VII

Preparation of
Di[1,3-dimethyl-3-(t-butylperoxy)butyl] succinate

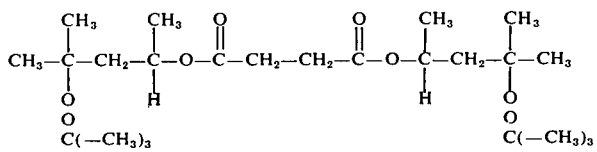

A mixture of 4.13 g. (0.02 mole) of 2-methyl-2-(t-butylperoxy)-4-pentanol (92%) and 1.5 g. (0.01 mole) of succinyl chloride and 25 ml. of diethyl ether was refluxed for 48 hours.

Evolution of hydrochloric acid could be detected as the mixture was refluxing. At the end of 48 hours no more HCl could be detected.

The mixture was stripped under reduced pressure. A slightly yellow colored liquid was obtained weighing 4.4 g.; theoretical yield 4.42 g.

The I.R. of the material was free of OH and C-Cl bands and contained the characteristic bands of the desired product.

EXAMPLE VIII

Preparation of Ethylene
Bis[1,3-dimethyl-3-(t-butylperoxy)-butyl carbonate]

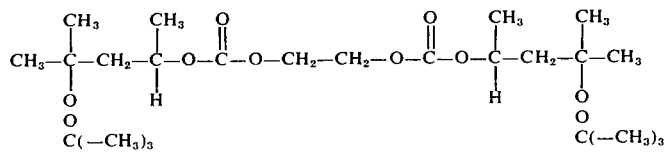

To a mixture of 29.4 g. (0.1 mole) of 1,3-dimethyl-3-(t-butylperoxy)butyl chloroformate (86.3%) and 3.6 g. (0.05 mole) of ethylene glycol in 26 ml. of acetone and 25 ml. of diethyl ether at 20± 1°C. was added a solution of 7.9 g. (0.1 mole) of pyridine in 10 ml. of diethyl ether. The mixture was allowed to react for 24 hours at 25± 1°C. At the end of this period the reaction mixture was filtered off from the pyridine hydrochloride and the organic phase washed with 100 ml. 10% solution of tartaric acid and water to neutrality. The ether solution was dried over anhydrous MgSO$_4$, filtered and the solvent evaporated under reduced pressure.

A yield of 15.2 g. was obtained. The I.R. of this material showed the characteristic bands of the desired compound with little contamination of hydroxyl-containing material.

EXAMPLE IX

Preparation of di[1,3-dimethyl-3-(t-butylperoxy)butyl] ethyl phosphate

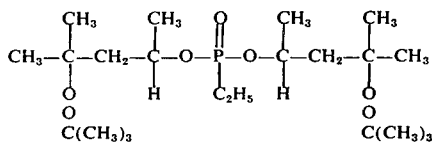

To a mixture of 22.1 g. (0.1 mole) of 2-methyl-2-(t-butylperoxy)-4-pentanol (86%) and 7.9 g. (0.1 mole) of pyridine in 50 ml. of diethyl ether cooled at 5± 1°C. was added a solution of 8.14 g. (0.05 mole) of ethyl dichlorophosphonate in 10 ml. of diethyl ether.

After the addition was completed the reaction mixture was allowed to stir at 25± 1°C. for 24 hours.

At the end of this time the reaction mixture was filtered from the pyridine hydrochloride and it was washed with 10% solution of tartaric acid and water to neutrality. The ether solution was dried over anhydrous MgSO$_4$, filtered and the solvent evaporated under reduced pressure. A liquid was obtained (13 g.). The I.R. indicated that the desired product was prepared.

EXAMPLE X

Preparation of N,N'-m-phenylene
bis[1,3-dimethyl-3-(t-butyl-peroxy)butyl carbamate]

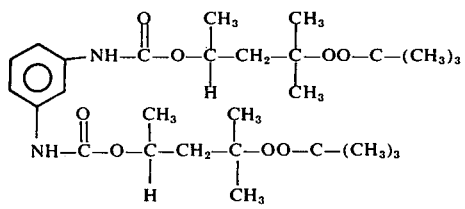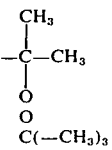

A mixture of 4.2 g. (0.02 mole) of 1,3-dimethyl-3-(t-butylperoxy)butanol (91%) and 1.6 g. (0.01 mole) of m-phenylenediisocyanate and few crystals of triethylene diamine and 40 ml. of hexane was placed into a dry flask, equipped with magnetic stirrer, thermometer, condenser and drying tube.

The mixture was allowed to stir for four hours at 50° to 60°C. At the end of this time the reaction mixture contained an insoluble organic material.

This material was separated and the trace amount of solvent stripped under reduced pressure. A viscous liquid weighing 1.8 g. was obtained. The I.R. indicated that the desired product was obtained.

EXAMPLE XI

Preparation of
2,2-bis[3,3-di(t-butylperoxy)butoxy]propane

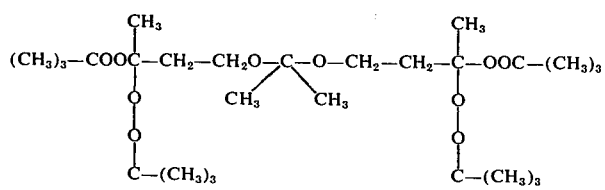

A mixture of 21.0 g. (0.08 mole) of 3,3-di(t-butylperoxy)butanol (96.6%), 4.2 g. (0.04 mole) of 2,2-dimethoxypropane, 25 ml. of benzene and 0.002 g. of p-toluensulfonic acid were combined and the mixture was distilled under atmospheric pressure. When 13 ml. of distillate boiling from 57° to 59°C. was collected, the distillation was stopped.

The pot residue was cooled down to 23° to 25°C. and neutralized with anhydrous $Na_2CO_3$. The mixture was filtered and the remaining solvent evaporated under reduced pressure. A liquid weighing 19.2 g. was obtained. The I.R. indicated that the desired product was prepared.

EXAMPLE XII

Preparation of
Bis(2[1,3-dimethyl-3-(t-butylperoxy)butoxycarbox-amido]ethyl) fumarate

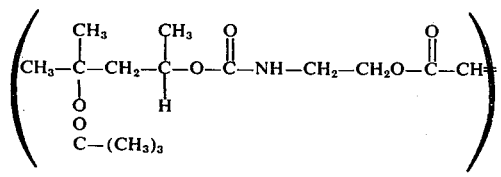

A mixture of 4.2 g. (0.02 mole) of 1,3-dimethyl-3-(t-butylperoxy)-4-pentanol and 2.5 g. (0.01 mole) of bis(2-isocyanoethyl) fumarate and 100 ml. of hexane was placed into a dry flask equipped with magnetic stirrer, thermometer, condenser and drying tube.

The mixture was allowed to stir for 8 hours at 50° to 60°C. At the end of this period the reaction mixture contained an insoluble organic material.

This material was separated and the trace amounts of solvent stripped under reduced pressure.

A viscous liquid weighing 5.2 g. was obtained. The I.R. indicated that the desired product was obtained.

EXAMPLE XIII

Crosslinkable Compositions

A mixture of the desired polymeric material and 0.01 mole of the difunctional coupled compound is blended together on a standard roll mill, such as used in the rubber industry. The mixture is removed from the roll mill and a portion is placed in a press mold and heat cured at a determined temperature for a period of 20 minutes.

The slabs are permitted to cool down and mature at room temperature for 24 hours. The mature slabs were then cut into dumbell shaped samples and tested for tensile strength on an Instron Tensile Tester, following ASTM procedure as described in D412-61T "Tension Testing of Vulcanized Rubber" or the crosslinking in the case of polyethylene is determined by the solvent extraction procedure. In addition to the polymer-peroxide mixture, the crosslinkable mixture, may contain co-agents such as sulfur, promoters, fillers, and reinforcing materials. Desirable fillers are carbon black, titanium dioxide, clacium silicate and alkaline earth metal carbonates.

In Table I the crosslinking ability of the coupled compounds of our invention in polyethylene are compared to a hydroxy-containing peroxide and to difunctional peroxides. Tables II, III, and IV show the versatility of the product of our invention in urethane rubber, ethylene-propylene rubber and silicone rubber.

Table I

CROSSLINKING OF POLYETHYLENE
The polyethylene used for this test was a low density polyethylene called Bakelite DYNH-1, having the following physical properties:
 Melt index (ASTM Test D-1238) 190°C. 2.0g./10 min.
 Density (ASTM Test D-1505) 0.919
The crosslinking test was carried out at 340° and 375°F. for 30 minutes.

| Peroxides | Molar Equivs. (2) | % Crosslinking (1) 340°F. | 375°F. |
|---|---|---|---|
| Di[1,3-dimethyl-3-(t-butylperoxy)butyl] carbonate (Examples I, II, & III) | 0.010 | 89.3 | 89.7 |
| Di[1,3-dimethyl-3-(t-butylperoxy)butyl] succinate (Examples VII) | 0.010 | 88.9 | 89.2 |
| Ethylene bis[1,3-dimethyl-3-(t-butylperoxy)-butyl carbonate] (Example VIII) | 0.010 | 87.9 | 87.4 |
| 2-Methyl-2-(t-butylperoxy)-4-pentanol | 0.015 | 78.4 | 75.4 |
| 2,5-dimethyl-2,5-di(t-butylperoxy)-hexane | 0.010 | 85.9 | 84.5 |

Table I-continued
CROSSLINKING OF POLYETHYLENE

The polyethylene used for this test was a low density polyethylene called Bakelite DYNH-1, having the following physical properties:
- Melt index (ASTM Test D-1238) 190°C. 2.0g./10 min.
- Density (ASTM Test D-1505) 0.919

The crosslinking test was carried out at 340° and 375°F. for 30 minutes.

| Peroxides | Molar Equivs. (2) | % Crosslinking (1) 340°F. | 375°F. |
|---|---|---|---|
| 2,5-dimethyl-2,5-di(t-butylperoxy)-hexyne-3 | 0.010 | 81.8 | 84.9 |
| 2,5-dimethyl-2,5-di(t-butylperoxy)-hexane | 0.015 | 89.3 | 88.0 |
| 2,5-dimethyl-2,5-di(t-butylperoxy)-hexyne-3 | 0.015 | 86.0 | 87.7 |

(1) The percentage crosslinking was determined by extraction of the crosslinked sample with refluxing xylene. In all cases the polyethylene charge was 100% extractable before crosslinking.
(2) Based on number of active oxygens per mole.

From the table it is obvious that the coupled compounds of our invention are more efficient than the hydroxy containing peroxide that they were derived from. This test also shows that the coupled compounds are significantly more efficient at equal molar equivalents than other difunctional peroxides that are commercially used to crosslink polyethylene.

Table II
VULCANIZATION OF URETHANE RUBBER FORMULATION

| | |
|---|---|
| Genthane-S (1) | 100 parts |
| H.A.F. Carbon Black (2) | 25 parts |
| Stearic acid | 0.2 parts |

The cure was carried out with 0.010 mole equivalent of peroxide at 340°F. for 30 minutes.

| Peroxides | (psi) 300% Modulus | (psi) Ult. Tensile | (psi) % Elongation |
|---|---|---|---|
| Di[1,3-dimethyl-3-(t-butylperoxy)butyl] carbonate (Examples I, II, and III) | 2091 | 4512 | 493 |
| Di[1,3-dimethyl-3-(t-butylperoxy)butyl] succinate (Example VII) | 1472 | 4167 | 575 |
| Ethylene bis[1,3-dimethyl-3-(t-butylperoxy) butyl carbonate] (Example VIII | 2419 | 3502 | 375 |

(1) Genthane-S is a designation given to one of the polyurethane elastomers derived from a polyester or developed by The General Tire & Rubber Company, having the following properties:
Mooney Viscosity (ML4' 212°F.) 50± 10
Specific Gravity 1.19
(2) H.A.F. Carbon Black is a high abrasion furnace black.
The urethane rubber charge without peroxide has 0 to 100 psi 300% modulus.

Table III
VULCANIZATION OF ETHYLENE-PROPYLENE RUBBER FORMULATION

| | |
|---|---|
| EPR-404 (1) | 100 parts |
| S.R.F. Carbon Black (2) | 60 parts |
| Sulfur | 0.33 parts |
| Peroxide | 0.010 mole equivalent |
| Cure Time | 30 minutes |
| Cure Temperature | 340°F. |

| Peroxides | (psi) 300% Modulus | (psi) Ult. Tensile | (psi) % Elongation |
|---|---|---|---|
| Di[1,3-dimethyl-3-(t-butylperoxy)butyl] carbonate (Examples I, II, and III) | 1004 | 2118 | 567 |
| Di[1,3-dimethyl-3-(t-butylperoxy)butyl] succinate (Example VII) | 715 | 2096 | 710 |
| Ethylene bis[1,3-dimethyl-3-(t-butylperoxy) butyl carbonate] (Example VIII) | 1089 | 2232 | 552 |

(1) E.P.R.-404 is an ethylene-propylene copolymer elastomeric material manufactured by Enjay, having specific gravity g/cc 0.86
Mooney Viscosity at 212°F. (8 minutes) 40
(2) S.R.F. Carbon Black is a semi-reinforcing furnace carbon black manufactured by Cabot Corporation.
Without peroxide ethylene-propylene rubber copolymer has a 300% Modulus of 0 to 100 psi.

Table IV
CROSSLINKING OF SILICONE RUBBER FORMULATION

| | |
|---|---|
| Silicone Rubber-404 (1) | 100 parts |
| Peroxide | 0.010 mole equivalents |
| Cure Temperature | 340°F. |
| Cure Time | 30 minutes |

| Peroxides | 300 Modulus | Ult. Tensile | % Elong. |
|---|---|---|---|
| Di[1,3-dimethyl-3-(t-butylperoxy)butyl] carbonate (Examples I, II, & III) | 478 | 871 | 431 |

(1) Silicone Rubber-404 is a general purpose reinforced silicone gum manufactured by General Electric.

The silicone rubber charge without peroxide has a 300% modulus of 0 psi.

EXAMPLE XIV

This example illustrates the use of the coupled peroxides of present disclosures as initiators of vinyl monomer polymerization. Compound [B] (from Example V) at a concentration of 5 × 10$^{-4}$ moles per deciliter of styrene, polymerized styrene at 100°C. at a rate of 6.20 × 10$^{-3}$ moles per liter per minute. When no initiator is present, the thermal polymerization of styrene at 100°C. proceeds at a rate of 2.82 × 10$^{-3}$ moles per liter per minute. Compound [A] (from Examples I, II, and III) at a concentration of 5 × 10$^{-4}$ moles per diciliter of styrene polymerized styrene 1.65 faster at 115°C. than the termal polymerization rate when no polymerization initiator is present.

EXAMPLE XV

Curing An Unsaturated Polyester-Styrene Resin With Coupled Peroxide

An unsaturated polyester resin was made by reacting maleic anhydride (1.00 mole), phthalic anhydride (1.0 mole), and propylene glycol (2.2 mole) until an acid number of 45–50 was obtained. To this was added hydroquinone at a 0.013% concentration. Seven parts of this unsaturated polyester was diluted with 3 parts of monomeric styrene to obtain a homogeneous blend having a viscosity of 13.08 poise and a specific gravity of 1.14. To 20 g. of this blend was added the 0.2 g. of the desired coupled peroxide and the resulting composition placed in a constant temperature bath at 115°C.

The internal temperature was recorded as function of time. The following results were obtained with some of the coupled compounds (Table V):

Table V

| | S.P.I. EXOTHERM AT 115°C. AND 1% CONCENTRATION IN POLYESTER RESIN PREPARED IN EXAMPLE VIII | | | |
|---|---|---|---|---|
| Peroxides | Gel Time In Min. | Cure Time In Min. | Peak In °F | Barcol Hardness |
| Di[1,3-dimethyl-3-(t-butylperoxy)-butyl] carbonate (Examples I, II, and III) | 9.5 | 11.1 | 455 | 45 |
| Ethylene bis[1,3-dimethyl-3-(t-butylperoxy)butyl carbonate] (Example VIII) | 10.8 | 12.8 | 450 | 45 |
| Di[2-(t-butylperoxycarbonyl)ethyl] carbonate (Example V) | 7.1 | 8.5 | 450 | 45 |

Without an initiator, no cure of this resin blend occured after more than 30 minutes at 115°C.

EXAMPLE XVI

Half-Life Comparisons of Coupled and Uncoupled Hydroxy-Peroxides (Carried out in Benzene at 0.1 molar concentrations)

| Peroxide | t½ Hours (°C) |
|---|---|
| 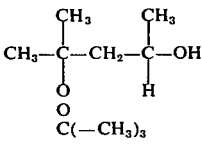<br>2-Methyl-2-(t-butylperoxy)-4-pentanol | 13.6 (115°C.) |
| 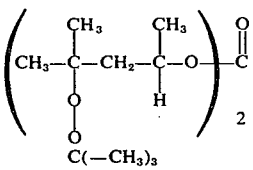<br>Di[1,3-dimethyl-3-(t-butylperoxy)butyl] carbonate (Examples I, II, & III) | 26.8 (115°C.) |
| 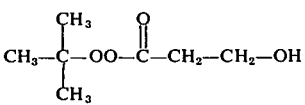<br>t-butylperoxy 3-hydroxypropionate | 13.0 (100°C.) |
| 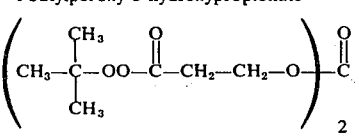<br>Di[2-(t-butylperoxycarbonyl)ethyl] carbonate (Example V) | 30.7 (100°C.) |

As can be seen from the half-life values, the peroxides containing hydroxyl have significantly lower half-lives than the coupled compounds. Thus, the coupled peroxides are more thermally stable and safer to handle, ship, store and use.

Thus having described the invention, what is claimed is:

1. In the process of crosslinking elastomers capable of being crosslinked by free radicals using as the crosslinking agent a free radical affording compound, the improvement which comprises using as said agent a peroxide of the formula R—W—R' where:
   a. W is selected from —C(=O)—, —C(=O)R$^4$C(=O)—, —C(=O)C(=O)—,

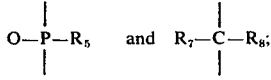

b. R and R' are identical and are selected from R$_3$OO—C(R$_1$)(R$_2$)—R$^3$O—, (R$_3$OO)$_2$C(R$_4$)—R$^2$O—, R$_3$OOC(=O)R$^3$O—, R$_3$OOC(=O)OR$^3$O—, R$_1$OC(=O)OO—C(R$_1$)(R$_2$)—R$^2$O—, and R$_1$C(=O)OO—C(R$_1$)(R$_2$)—R$^2$O—;
   c. R$_1$ and R$_2$ are aliphatic having 1–12 carbon atoms, cycloaliphatic having 3–12 carbon atoms, or aromatic having 6–12 carbon atoms;
   d. R$_3$ is aliphatic or cycloaliphatic, each having 4-10 carbon atoms and the carbon atom joined to the peroxy oxygen atom is a tertiary carbon atom;
   e. R$_4$ is aliphatic having 1–10 carbon atoms or cycloaliphatic having 3–12 carbon atoms;
   f. R$_5$ is lower alkyl, cycloalkyl, aryl, alkoxy, cycloalkoxy, aralkoxy, or aryloxy;
   g. R$_6$ is H or lower alkyl;
   h. Y is the diradical O, S, or N—R$_6$;
   j. R$^2$ is an aliphatic diradical having 1–10 carbon atoms or a cycloaliphatic diradical having 3–12 carbon atoms;
   k. R$^3$ is an aliphatic diradical having 1–10 carbon atoms, cycloaliphatic diradical having 3–12 carbon atoms, aromatic diradical having 6–12 carbon atoms, or araliphatic diradical having 7–16 carbon atoms;
   l. R$^4$ is selected from R$^3$, YR$^3$Y, R$^3$C(=O)YR$^3$YC(=O)R$^3$, YR$^3$YC(=O)YR$^3$YC(=O)YR$^3$Y, YR$^3$YC(=O)R$^3$C(=O)YR$^3$Y, YR$^3$C(=O)YR$^3$C(=O)YR$^3$Y, YR$^3$C(=O)YR$^3$YC(=O)R$^3$Y, YR$^3$YC(=O)YR$^3$Y, YR$^3$YC(=O)R$^3$Y and YR$^3$YR$^3$Y; and
   m. R$_7$ and R$_8$ are selected from H, alkyl of 1–10 carbons and cycloalkyl of 3–12 carbons and, when R$_7$ is H, R$_8$ can also be aryl of 6–12 carbons, and R$_7$ and R$_8$ when taken together form alkylene of 2–11 carbons.

2. A process as in claim 1 wherein the elastomer is polyurethane rubber.

3. A process as in claim 2 wherein the peroxide is di(1,3-dimethyl-3-(t-butylperoxy)butyl)carbonate.

4. A process as in claim 2 wherein the peroxide is di(1,3-dimethyl-3-(t-butylperoxy)butyl)succinate.

5. A process as in claim 2 wherein the peroxide is ethylene bis(1,3-dimethyl-3-(t-butylperoxy)butyl carbonate).

6. A process as in claim 1 wherein the elastomer is ethylene-propylene rubber.

7. A process as in claim 6 wherein the peroxide is di(1,3-dimethyl-3-(t-butylperoxy)butyl)carbonate.

8. A process as in claim 6 wherein the peroxide is di(1,3-dimethyl-3-(t-butylperoxy)butyl)succinate.

9. A process as in claim 6 wherein the peroxide is ethylene bis(1,3-dimethyl-3-(t-butylperoxy)butyl carbonate).

10. A process as in claim 1 wherein the elastomer is silicone rubber.

11. A process as in claim 10 wherein the peroxide is di(1,3-dimethyl-3-(t-butylperoxy)butyl)carbonate.

* * * * *

UNITED STATES PATENT OFFICE
CERTIFICATE OF CORRECTION

Patent No. 3,963,673  Dated June 15, 1976

Inventor(s) Antonio Joseph D'Angelo  Orville Leonard Mageli  Chester Stephen Sheppard It is certified that error appears in the above-identified patent and that said Letters Patent are hereby corrected as shown below:

Claim 1, line 50

$R_5$ is lower alkyl, cycloalkyl, aryl, alkoxy, cycloalkoxy, aralkoxy, or aryloxy;

SHOULD READ $R_5$ is lower alkyl, cycloalkyl, aralkyl, aryl, alkoxy, cycloalkoxy, aralkoxy, or aryloxy;

Signed and Sealed this

Seventh Day of September 1976

[SEAL]

Attest:

RUTH C. MASON
*Attesting Officer*

C. MARSHALL DANN
*Commissioner of Patents and Trademarks*